US012636168B1

(12) United States Patent
Chen et al.

(10) Patent No.: US 12,636,168 B1
(45) Date of Patent: May 26, 2026

(54) EXPANDABLE INTERVERTEBRAL FUSION CAGE

(71) Applicant: NATIONAL FORMOSA UNIVERSITY, Huwei Township (TW)

(72) Inventors: Shou-I Chen, Huwei Township (TW); Hsin-Yi Lin, Huwei Township (TW); Yi-Kai Chen, Huwei Township (TW); Yu-Hsu Chen, Huwei Township (TW); Mu-Kuang He, Huwei Township (TW); Chuan-Ching Huang, Huwei Township (TW); Jui-Yo Hsu, Huwei Township (TW)

(73) Assignee: NATIONAL FORMOSA UNIVERSITY, Huwei Township (TW)

( * ) Notice: Subject to any disclaimer, the term of this patent is extended or adjusted under 35 U.S.C. 154(b) by 0 days.

(21) Appl. No.: 19/289,598

(22) Filed: Aug. 4, 2025

(51) Int. Cl.
　　*A61F 2/44*　　　(2006.01)
　　*A61F 2/30*　　　(2006.01)

(52) U.S. Cl.
　　CPC .... *A61F 2/447* (2013.01); *A61F 2002/30176* (2013.01); *A61F 2002/30326* (2013.01); *A61F 2002/30359* (2013.01); *A61F 2002/30405* (2013.01); *A61F 2002/3055* (2013.01)

(58) Field of Classification Search
　　CPC ............................... A61F 2/4455; A61F 2/447
　　See application file for complete search history.

(56) References Cited

U.S. PATENT DOCUMENTS

| | | | | | |
|---|---|---|---|---|---|
| 9,566,168 | B2 * | 2/2017 | Glerum | .................... | A61F 2/447 |
| 9,913,727 | B2 * | 3/2018 | Thommen | ............... | A61F 2/447 |
| 11,166,826 | B2 * | 11/2021 | Huang | .................... | A61F 2/447 |
| 11,602,440 | B2 * | 3/2023 | Zakelj | .................... | A61F 2/4611 |
| 12,011,364 | B2 * | 6/2024 | Gray | ..................... | A61F 2/4611 |
| 12,329,652 | B2 * | 6/2025 | Shoshtaev | ............. | A61F 2/4611 |
| 12,396,867 | B2 * | 8/2025 | Gray | .................... | A61F 2/4455 |

(Continued)

*Primary Examiner* — Nicholas W Woodall

(74) *Attorney, Agent, or Firm* — Birch, Stewart, Kolasch & Birch, LLP

(57) ABSTRACT

An expandable intervertebral fusion cage, wherein each first block and second block of the fusion assembly is provided with a receiving groove, and the bottom of the groove includes an inclined surface. An intermediate block is installed within the receiving groove. The control assembly includes a fixing member, a pressing member, a horizontal adjustment rod, and a vertical adjustment rod. The fixing member is disposed at the front end of the fusion assembly and positioned between the first block and the second block, while the pressing member is disposed at the rear end and positioned against the intermediate block. The horizontal adjustment rod extends through the fixing member and is pivotally connected to a pushing member, enabling control of the horizontal outward movement of the fusion assembly. One end of the vertical adjustment rod passes through the horizontal adjustment rod and is threadably engaged with the pressing member, while the other end extends beyond the horizontal adjustment rod. Rotation of the vertical adjustment rod drives the pressing member, which actuates the intermediate block to expand the first block and the second block, resulting in relative vertical outward displacement. Accordingly, the width and height of the fusion cage can be independently adjusted as needed, thereby enhancing its applicability.

10 Claims, 5 Drawing Sheets

(56) References Cited

U.S. PATENT DOCUMENTS

| | | | |
|---|---|---|---|
| 12,458,509 B2 * | 11/2025 | Corrao, Jr. ............ | A61F 2/4455 |
| 2004/0049271 A1 * | 3/2004 | Biedermann ............. | A61F 2/44 |
| | | | 623/17.11 |
| 2017/0209282 A1 * | 7/2017 | Aghayev ................. | A61F 2/447 |
| 2020/0163775 A1 * | 5/2020 | Kim ........................ | A61F 2/447 |
| 2022/0395381 A1 * | 12/2022 | Valkoun ................. | A61F 2/447 |
| 2025/0161064 A1 * | 5/2025 | Rolf ....................... | A61B 17/80 |
| 2025/0359999 A1 * | 11/2025 | Valkoun ............... | A61F 2/4455 |

\* cited by examiner

EXPANDABLE INTERVERTEBRAL FUSION CAGE

BACKGROUND OF THE DISCLOSURE

1. Field of the Disclosure

The present invention relates to an expandable intervertebral fusion cage, and more particularly, to an expandable intervertebral fusion cage capable of independent adjustment and expansion in different directions to support intervertebral spacing.

2. Description of the Prior Art

The human spine is composed of multiple vertebral bodies arranged sequentially. The entire spinal column consists of multiple pairs of adjacent vertebral bodies, with intervertebral discs positioned between each adjacent pair. The intervertebral discs provide support for the vertebral bodies, preventing compression of adjacent nerves or blood vessels. Due to external forces, prolonged poor posture, or normal aging processes, adjacent vertebral bodies may become compressed, causing intervertebral disc herniation. Such conditions result in adjacent vertebral bodies moving closer together, potentially compressing nearby nerves or blood vessels, leading to discomfort such as soreness, pain, or numbness.

With advancements in medical technology, intervertebral fusion surgery has become a common solution for treating conditions like intervertebral disc herniation and vertebral compression. Typically, this procedure involves removing the intervertebral disc and placing a spacer or cage between adjacent vertebral bodies to maintain spacing and alleviate nerve or blood vessel compression symptoms.

Conventional technology, such as disclosed in US patent No. US2023/0372116A1, reveals an adjustable-height fusion cage. However, this cage can only adjust in one direction, lacking the capability to adjust width perpendicular to this direction. Consequently, the width of the cage must be pre-adjusted before insertion between vertebral bodies, making implantation difficult if the cage is too wide. Once placed, the width cannot be adjusted further, limiting the cage's ability to effectively support varying intervertebral spacing needs. Upon closer inspection, these conventional structures exhibit clear shortcomings, primarily due to their inability to adjust dimensions in multiple directions, substantially reducing their effectiveness in maintaining intervertebral spacing.

In view of the above, based on extensive experience in manufacturing, developing, and designing related products, the inventor has meticulously designed and carefully evaluated the present invention, which effectively addresses the aforementioned shortcomings and possesses enhanced practical applicability.

SUMMARY OF THE DISCLOSURE

The technical problem intended to be solved by the present invention is to provide an expandable intervertebral fusion cage, addressing the aforementioned shortcomings existing in the prior art.

Two fusion assembly are provided, each including a first block, a second block, and an intermediate block. The first block and the second block each have at least one receiving groove, and at least one inclined surface is formed at the bottom of each receiving groove. The intermediate block is installed within the receiving groove of the first block and the second block, and symmetrically provided with at least one tapered surface. The tapered surface of the intermediate block abuts against the inclined surface. Furthermore, a control assembly is included, which comprises a fixing member, a pressing member, a horizontal adjustment rod, and a vertical adjustment rod. The fixing member is disposed at the front ends of the two fusion assembly, and positioned between two of the first block and two of the second block. The pressing member is located at the rear ends of the fusion assembly, abutting against the intermediate block. The horizontal adjustment rod penetrates and is positioned by the fixing member, and is pivotally connected with two pushing member. The two pushing member are respectively connected to the first block of each fusion assembly. When the horizontal adjustment rod is rotated, the pushing member drives the two fusion assembly to move horizontally away from each other. One end of the vertical adjustment rod passes through the horizontal adjustment rod and is threadably engaged with the pressing member, while the other end of the vertical adjustment rod extends beyond the horizontal adjustment rod. Rotation of the vertical adjustment rod moves the pressing member toward the fixing member, simultaneously driving the intermediate block. The tapered surface of the intermediate block consequently expands the first block and the second block, causing them to move vertically away from each other.

The receiving groove has a limiting surface formed on each side of the inclined surface. The intermediate block is provided with at least two restricting portion, which abut against the limiting surface, thereby restricting the relative displacement of the first block and the second block to vertical movement only.

The first block includes at least one insertion pin, and the second block includes at least one insertion slot. The first block and the second block engage each other through insertion of the insertion pin into the insertion slot, thus restricting their relative displacement to horizontal movement only.

The pushing member comprises a fixed arm and a movable arm. One end of the fixed arm is secured to the horizontal adjustment rod, and the other end is pivotally connected to the movable arm by a first pivot point. The movable arm is pivotally connected to the first block by a second pivot point. When rotating the horizontal adjustment rod to control the pushing member, the fixed arm actuates the movable arm, applying a pushing force toward the second pivot point.

The fixing member includes a plurality of v-shaped groove, and each of the first block and the second block includes a guiding inclined surface. When the two fusion assembly horizontally move away from each other, the guiding inclined surface abuts against the v-shaped groove.

The pressing member is provided with two pushing portion, and the intermediate block includes a driven portion. The pressing member contacts the driven portion respectively via the pushing portion, thereby driving the intermediate block.

The inclined surface causes the receiving groove to become shallower toward the front end of the fusion assembly.

The length of the inclined surface is greater than that of the tapered surface.

One end of the horizontal adjustment rod positioned at the fixing member forms a gripping portion, while the other end protrudes from the fixing member to form a retaining ring. Further, the gripping portion is equipped with a stopper, such that the stopper and the retaining ring cooperatively limit axial displacement between the horizontal adjustment rod and the fixing member.

One end of the vertical adjustment rod is formed with a threaded portion that threadably engages the pressing member, while the other end of the vertical adjustment rod is enlarged to form a head portion. The head portion is dimensioned to be unable to pass through the horizontal adjustment rod, thereby axially limiting the position of the vertical adjustment rod to one side of the fixing member.

A primary objective of the present invention is to provide an intervertebral fusion cage capable of independently adjusting horizontal expansion between the two fusion assembly, as well as independently adjusting vertical expansion between the first block and the second block, through the operation of either the horizontal adjustment rod or the vertical adjustment rod. Consequently, the cage can adopt multiple volumetric configurations, significantly enhancing its applicability for treating diverse spinal conditions in different patients, and thereby greatly increasing its clinical usefulness.

A second primary objective of the present invention is that the vertical adjustment rod passes through the horizontal adjustment rod to control coordinated movement of the pressing member and the intermediate block, achieving vertical expansion of the intervertebral fusion cage. Furthermore, the horizontal adjustment rod controls horizontal expansion by driving the two fusion assembly through the pushing member. This structural arrangement efficiently achieves independent horizontal and vertical expansion with a minimal number of components, reducing the overall volume of the fusion cage and facilitating its placement between patient vertebrae.

Other objectives, advantages, and novel features of the present invention will become more apparent from the detailed description provided below in conjunction with the accompanying drawings.

BRIEF DESCRIPTION OF THE DRAWINGS

The present invention will be best understood by referring to the following detailed description of one illustrative embodiment in conjunction with the accompanying drawings, in which.

DETAILED DESCRIPTION

Figure 1:
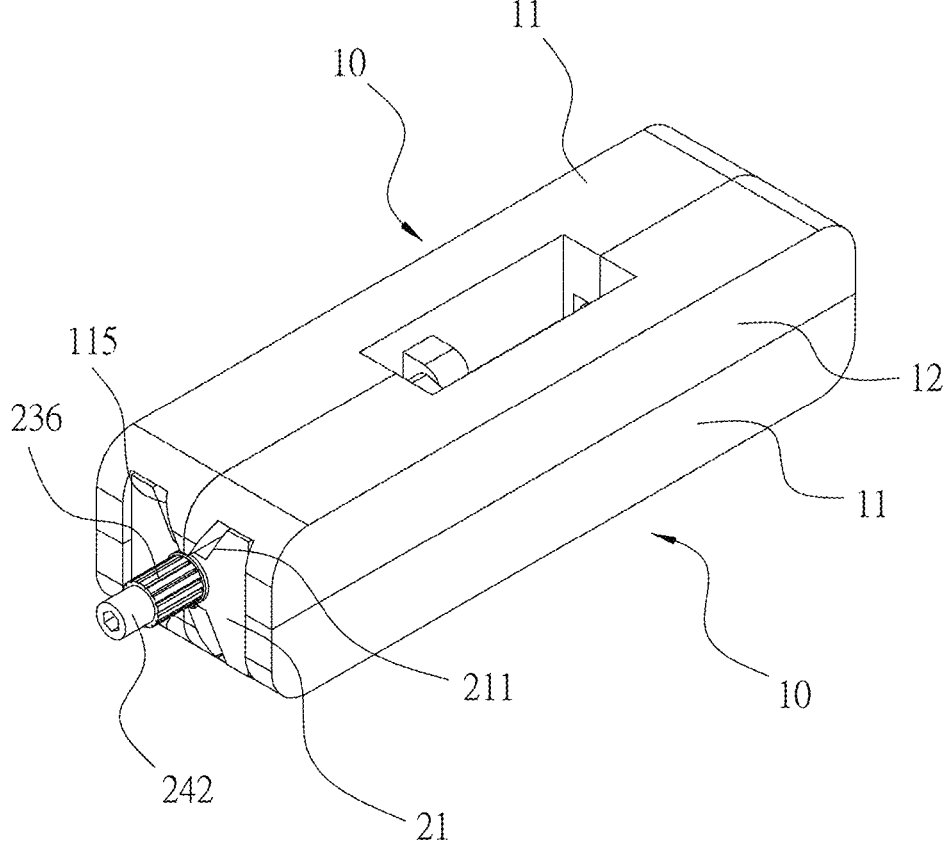
FIG. 1 is a perspective view of the present invention.
Figure 2:
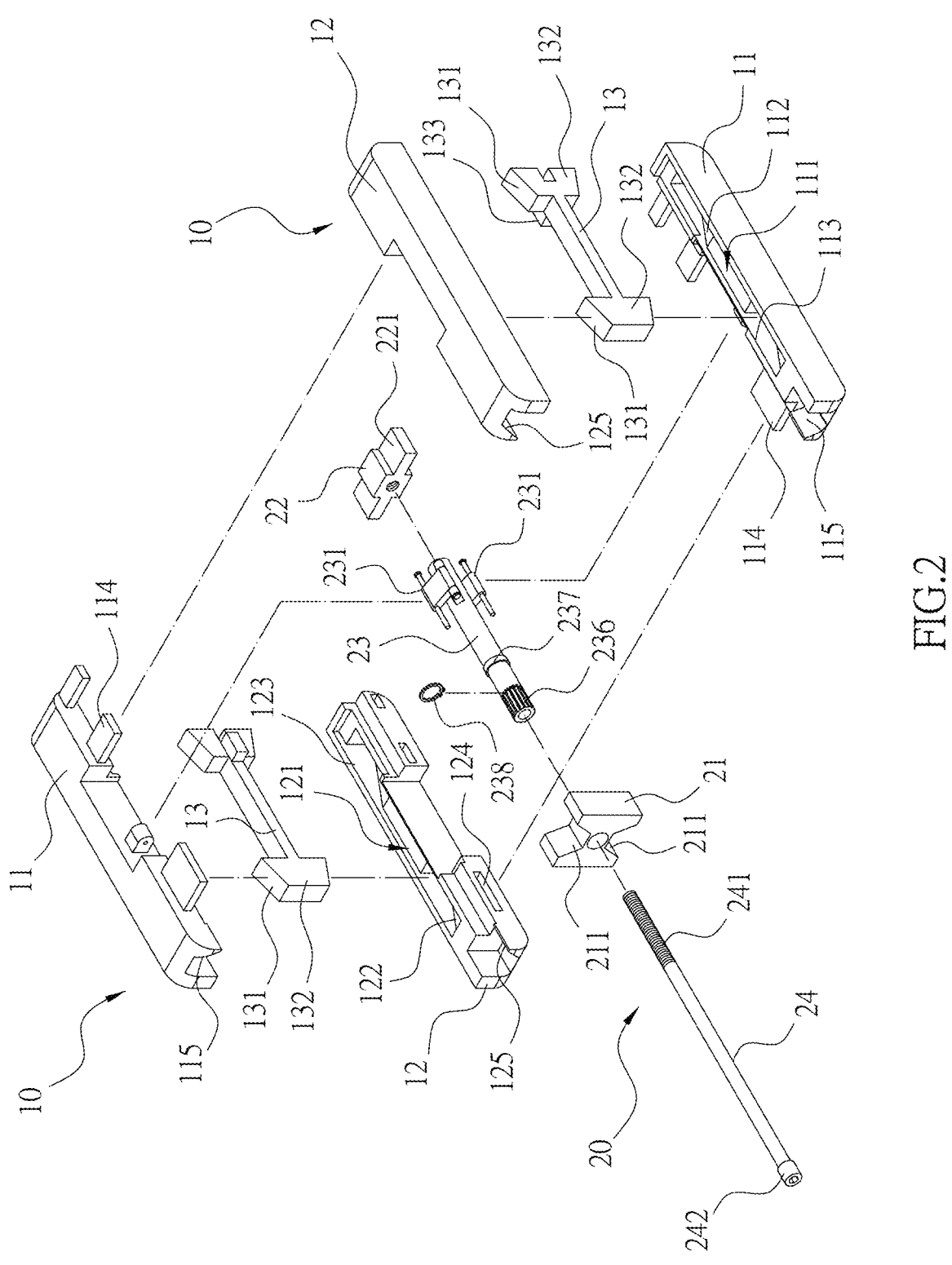
FIG. 2 is an exploded perspective view of the present invention.
Figure 3:
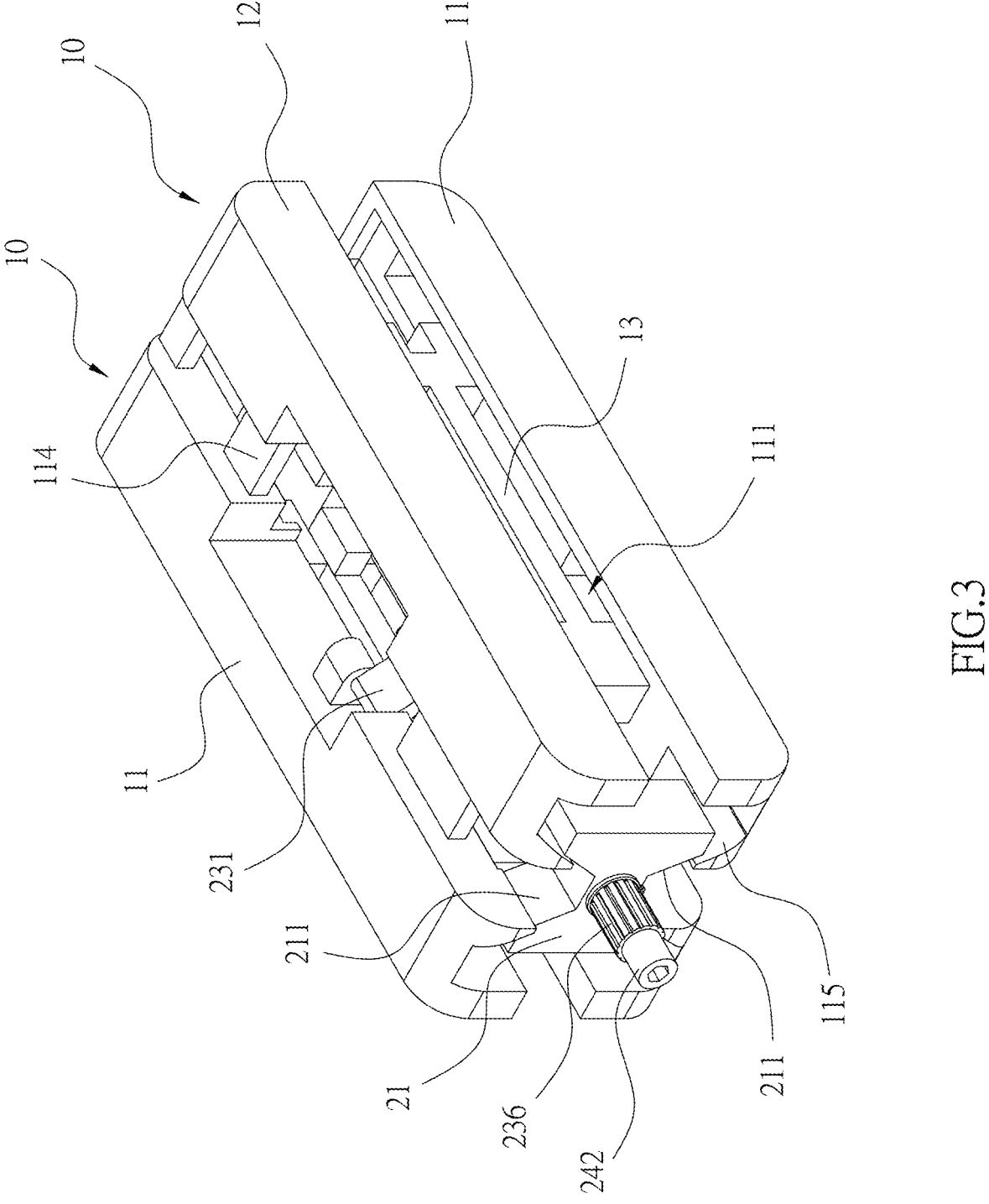
FIG. 3 is a perspective view of the present invention in an expanded state.
Figure 4:
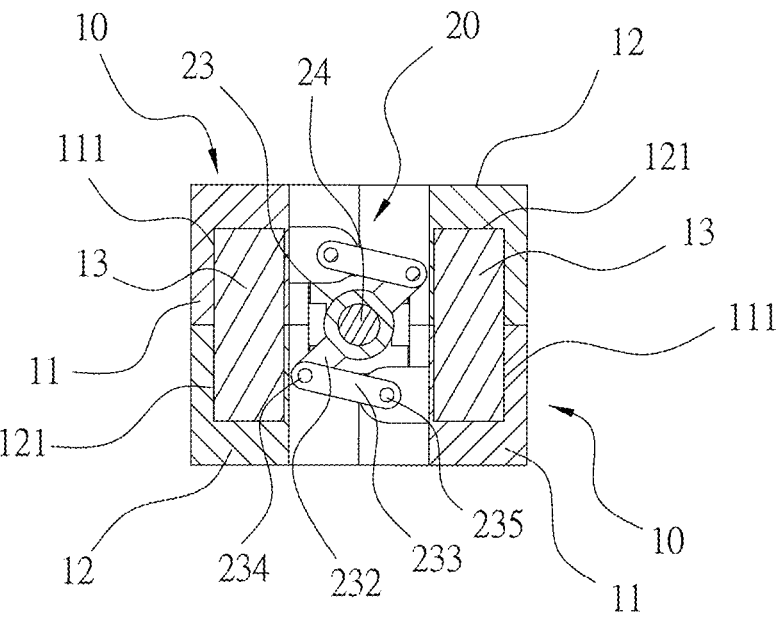
FIG. 4 is a cross-sectional view of the present invention in a contracted state.
Figure 5:
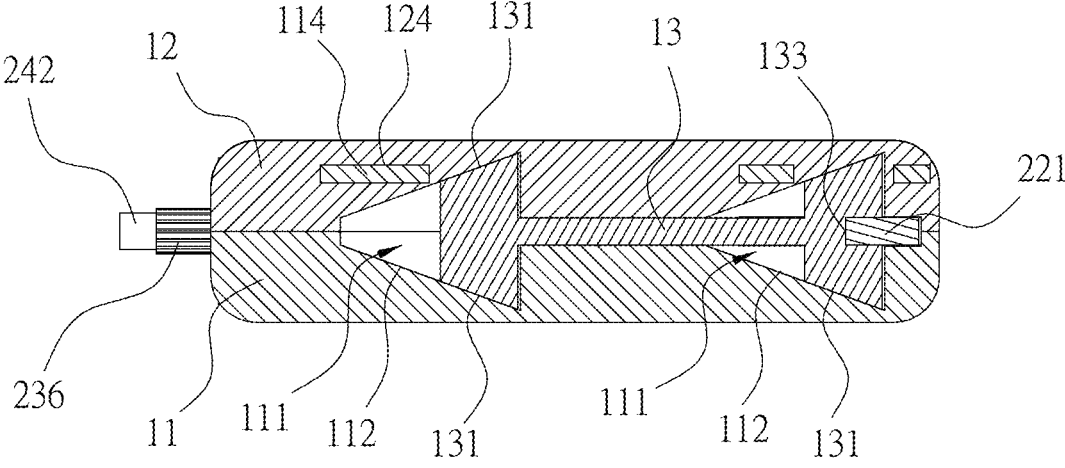
FIG. 5 is a longitudinal sectional view of the present invention in a contracted state.

Referring sequentially to FIG. 1 through FIG. 5, an expandable intervertebral fusion cage comprises two fusion assembly 10, each including a first block 11, a second block 12, and an intermediate block 13. The first block 11 and the second block 12 each define at least one receiving groove 111, 121, respectively, with at least one inclined surface 112, 122 formed at the bottom thereof. The intermediate block 13 is disposed within the receiving groove 111, 121 of the first block 11 and the second block 12, and is symmetrically provided with at least one tapered surface 131 abutting against the corresponding inclined surface 112, 122. Further provided is a control assembly 20, including a fixing member 21, a pressing member 22, a horizontal adjustment rod 23, and a vertical adjustment rod 24. The fixing member 21 is disposed at the front ends of the two fusion assembly 10, and positioned between two first blocks 11 and two second blocks 12. The pressing member 22 is located at the rear ends of the fusion assembly 10, abutting against the intermediate block 13. The horizontal adjustment rod 23 penetrates and is positioned by the fixing member 21, pivotally connected to two pushing member 231. The two pushing member 231 are respectively connected to the first block 11 of each fusion assembly 10. One end of the vertical adjustment rod 24 passes through the horizontal adjustment rod 23 and is threadably engaged with the pressing member 22, while the other end of the vertical adjustment rod 24 extends beyond the horizontal adjustment rod 23. In operation, rotation of the horizontal adjustment rod 23 actuates the two pushing member 231, causing horizontal outward displacement of the two fusion assembly 10 relative to each other. Similarly, rotation of the vertical adjustment rod 24 moves the pressing member 22 toward the fixing member 21, simultaneously driving the intermediate block 13. Consequently, the tapered surface 131 of the intermediate block 13 expands the first block 11 and the second block 12, causing vertical outward displacement relative to each other. Thus, independent operation of the horizontal adjustment rod 23 and the vertical adjustment rod 24 enables the fusion cage to be selectively expanded horizontally and vertically, effectively enhancing its applicability.

Figure 6:
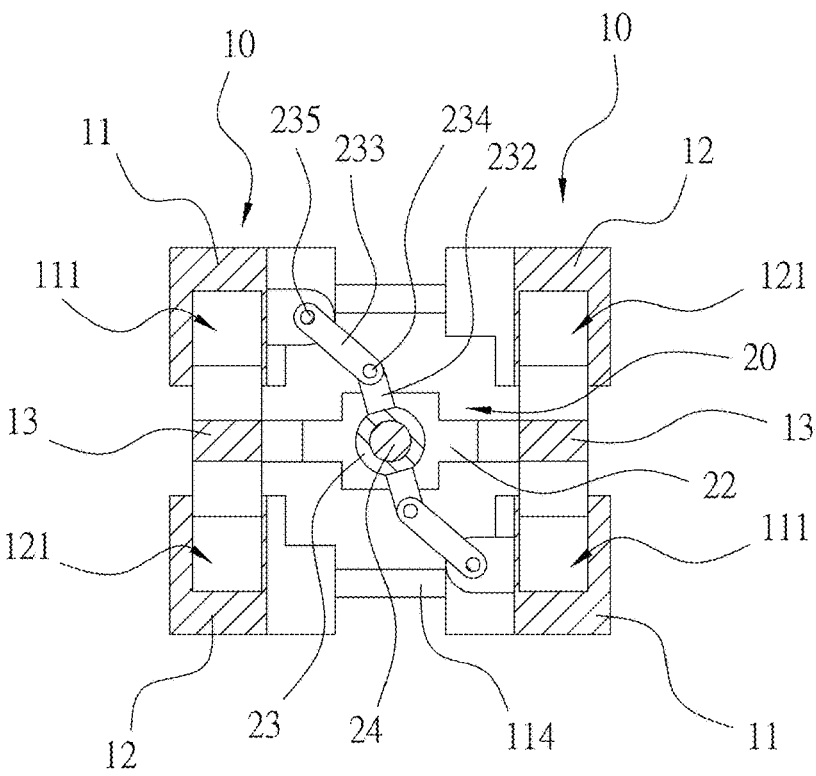
FIG. 6 is a cross-sectional view of the present invention in an expanded state.
Figure 7:
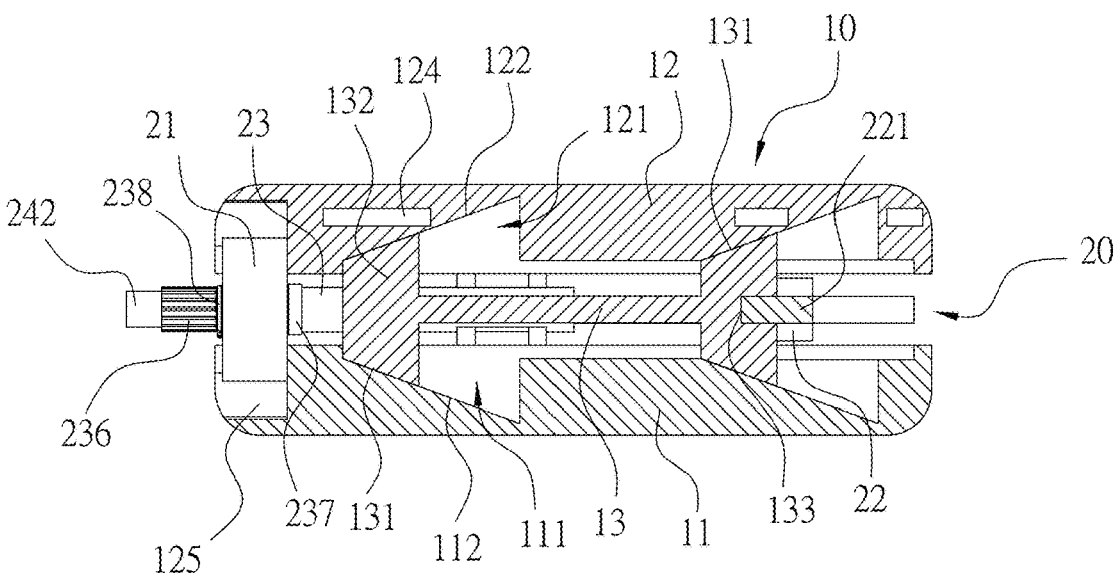
FIG. 7 is a longitudinal sectional view of the present invention in an expanded state.

Further describing the vertical expansion feature with reference to FIG. 2 through FIG. 7, one end of the vertical adjustment rod 24 is formed with a threaded portion 241 threadably engaged with the pressing member 22, and the other end of the vertical adjustment rod 24 is enlarged to form a head portion 242. The head portion 242 cannot pass through the horizontal adjustment rod 23, thus axially limiting the vertical adjustment rod 24 to one side of the fixing member 21. When rotating the head portion 242, the vertical adjustment rod 24 rotates in place due to axial restriction by the fixing member 21, while the pressing member 22 is prevented from rotation by its engagement with the intermediate block 13. Consequently, the pressing member 22 moves toward the fixing member 21 driven by the threaded portion 241. The pressing member 22 further includes two pushing portion 221, and the intermediate block 13 is provided with a driven portion 133. Each pushing portion 221 respectively contacts the corresponding driven portion 133 to actuate the intermediate block 13. Additionally, the inclined surface 112, 122 is configured such that the depth of the receiving groove 111, 121 gradually decreases toward the front end of the fusion assembly 10, and the length of each inclined surface 112, 122 exceeds that of the tapered surface 131. Thus, when the pressing member 22 is driven by the vertical adjustment rod 24, the two pushing portion 221 push the driven portion 133 of the two intermediate block 13, respectively, causing the intermediate block 13 to urge the first block 11 and the second block 12 vertically apart. Moreover, each receiving groove 111, 121 has a limiting surface 113, 123 on both sides of the corresponding inclined surface 112, 122, and the intermediate block 13 includes at least two restricting portion 132 abutting against the corresponding limiting surface 113, 123, thereby restricting relative movement between the first block 11 and the second block 12 solely to vertical displacement. Accordingly, the tapered surface 131 of the intermediate block 13 acts on the inclined surface 112, 122 of the first block 11 and the second block 12, effectively achieving independent vertical height expansion of the intervertebral fusion cage.

Further illustrating the horizontal expansion functionality, with reference to FIG. 2 through FIG. 7, the horizontal adjustment rod 23 is formed with a gripping portion 236 at one end adjacent to the fixing member 21, and a retaining ring 237 protrudes from the other end of the fixing member 21. Additionally, the gripping portion 236 is equipped with a stopper 238, which together with the retaining ring 237, limits axial displacement of the horizontal adjustment rod 23 relative to the fixing member 21. During assembly, the horizontal adjustment rod 23 is first passed through the fixing member 21 until the retaining ring 237 abuts the fixing member 21, and subsequently, the stopper 238 is secured onto the gripping portion 236, thus completing assembly rapidly. When rotating the gripping portion 236, the horizontal adjustment rod 23 is permitted only to rotate in place relative to the fixing member 21. Furthermore, the first block 11 includes at least one insertion pin 114, and the second block 12 includes at least one insertion slot 124, wherein the mutual insertion of the insertion pin 114 into the insertion slot 124 restricts relative displacement between the first block 11 and the second block 12 exclusively to horizontal movement. Moreover, the pushing member 231 comprises a fixed arm 232 and a movable arm 233. One end of the fixed arm 232 is fixed to the horizontal adjustment rod 23, while the other end of the fixed arm 232 pivotally connects the movable arm 233 through a first pivot point 234. The movable arm 233 pivotally connects to the first block 11 via a second pivot point 235. When the horizontal adjustment rod 23 is rotated to actuate the pushing member 231, the fixed arm 232 drives the movable arm 233, applying a pushing force toward the second pivot point 235, causing relative outward horizontal displacement between the two fusion assembly 10. Additionally, the fixing member 21 is provided with a plurality of v-shaped groove 211, and the first block 11 and the second block 12 each include a corresponding guiding inclined surface 115, 125. When the two fusion assembly 10 horizontally move apart, the guiding inclined surface 115, 125 engage the v-shaped groove 211. Thus, when adjusted to the expanded position, the fixing member 21 provides sufficient support through the engagement of the v-shaped groove 211 with the guiding inclined surface 115, 125, effectively preventing inadvertent sliding of the first block 11 and the second block 12, thereby enhancing the stability of the device during use.

With the structural features of the aforementioned specific embodiments, the following advantages can be achieved: by operating the horizontal adjustment rod 23 or the vertical adjustment rod 24, the intervertebral fusion cage is capable of independently performing horizontal expansion between the two fusion assembly 10, as well as independently achieving vertical expansion between the first block 11 and the second block 12. Consequently, the cage can offer numerous volumetric variations, effectively adapting to diverse spinal conditions of different patients, thereby significantly enhancing its practical applicability. Furthermore, the vertical adjustment rod 24 passes through the horizontal adjustment rod 23, controlling coordinated movement between the pressing member 22 and the intermediate block 13, thus achieving height expansion of the fusion cage. Additionally, the horizontal adjustment rod 23 drives horizontal expansion of the fusion cage by actuating the two fusion assembly 10 through the pushing member 231. Such structural arrangement effectively achieves independent horizontal and vertical expansion functionality with fewer components, thus enabling reduction of the overall volume of the fusion cage and facilitating its implantation within patient intervertebral spaces.

While the above description details preferred embodiments of the present invention, it should not be construed as limiting the scope thereof. Rather, all equivalent variations and modifications made according to the claims of the present invention should remain within the scope covered by the patent claims.

What is claimed is:

1. An expandable intervertebral fusion cage, comprising:
two fusion assembly, each comprising a first block, a second block, and an intermediate block, wherein the first block and the second block are each provided with at least one receiving groove, and at least one inclined surface is formed at the bottom of the receiving groove, the intermediate block is installed within the receiving groove of the first block and the second block, and the intermediate block is symmetrically provided with at least one tapered surface that abuts against the inclined surface; and
a control assembly comprising a fixing member, a pressing member, a horizontal adjustment rod, and a vertical adjustment rod, wherein the fixing member is disposed at the front end of the two fusion assembly and positioned between the two first block and the two second block, the pressing member is located at the rear end of the fusion assembly and positioned against the intermediate block, the horizontal adjustment rod passes through and is positioned within the fixing member, and is pivotally connected to two pushing member, the two pushing member being respectively connected to the first block of each fusion assembly, such that rotation of the horizontal adjustment rod controls the pushing member to drive the two fusion assembly in opposite horizontal directions, and one end of the vertical adjustment rod passes through the horizontal adjustment rod and is threadably engaged with the pressing member, while the other end extends beyond the horizontal adjustment rod, such that rotation of the vertical adjustment rod controls the pressing member to move toward the fixing member, and simultaneously drives the intermediate block, causing the tapered surface of the intermediate block to expand the first block and the second block vertically apart.

2. The expandable intervertebral fusion cage of claim 1, wherein a limiting surface is formed on both sides of the inclined surface of the receiving groove, and the intermediate block is provided with at least two restricting portion that abut against the limiting surface to restrict the first block and the second block to relative vertical displacement only.

3. The expandable intervertebral fusion cage of claim 1, wherein the first block includes at least one insertion pin, and the second block includes at least one insertion slot, such that the first block and the second block are mutually inserted to restrict them to relative horizontal displacement only.

4. The expandable intervertebral fusion cage of claim 1, wherein the pushing member comprises a fixed arm and a movable arm, one end of the fixed arm being fixed to the horizontal adjustment rod, and the other end being pivotally connected to the movable arm via a first pivot point, and the movable arm being pivotally connected to the first block via a second pivot point, such that rotation of the horizontal adjustment rod actuates the pushing member by transmitting a pushing force from the fixed arm to the movable arm in the direction of the second pivot point.

5. The expandable intervertebral fusion cage of claim 1, wherein the fixing member is formed with a plurality of v-shaped groove, and each of the first block and the second block is formed with a guiding inclined surface, such that when the two fusion assembly are horizontally displaced relative to each other, the guiding inclined surface is pressed against the v-shaped groove.

6. The expandable intervertebral fusion cage of claim 1, wherein the pressing member is provided with two pushing portion, and the intermediate block is provided with a driven portion, such that the pressing member drives the intermediate block by engaging the driven portion with the respective pushing portion.

7. The expandable intervertebral fusion cage of claim 1, wherein the inclined surface causes the receiving groove to gradually become shallower toward the front end of the fusion assembly.

8. The expandable intervertebral fusion cage of claim 1, wherein the sloped length of the inclined surface is greater than that of the tapered surface.

9. The expandable intervertebral fusion cage of claim 1, wherein one end of the horizontal adjustment rod located at the fixing member is formed with a gripping portion, and the other end of the fixing member is protrudingly provided with a retaining ring, and the gripping portion is equipped with a stopper, such that the stopper and the retaining ring cooperatively form a positioning limit between the horizontal adjustment rod and the fixing member.

10. The expandable intervertebral fusion cage of claim 1, wherein one end of the vertical adjustment rod is formed with a threaded portion that is threadably engaged with the pressing member, and the other end of the vertical adjustment rod is enlarged to form a head portion, the head portion being unable to pass through the horizontal adjustment rod, thereby being axially retained at one side of the fixing member.

\* \* \* \* \*